United States Patent
Liao et al.

(10) Patent No.: US 10,501,797 B2
(45) Date of Patent: Dec. 10, 2019

(54) NONINVASIVE PRENATAL DIAGNOSIS OF FETAL TRISOMY BY ALLELIC RATIO ANALYSIS USING TARGETED MASSIVELY PARALLEL SEQUENCING

(71) Applicant: The Chinese University of Hong Kong, Shatin (CN)

(72) Inventors: Jiawei Liao, Tai Po Market (CN); Kwan Chee Chan, Shatin (CN); Wai Kwun Rossa Chiu, Shatin (CN); Yuk Ming Dennis Lo, Homantin (CN)

(73) Assignee: The Chinese University of Hong Kong, Shatin, New Territories (HK)

( * ) Notice: Subject to any disclaimer, the term of this patent is extended or adjusted under 35 U.S.C. 154(b) by 640 days.

(21) Appl. No.: 15/076,455

(22) Filed: Mar. 21, 2016

(65) Prior Publication Data

US 2016/0201134 A1 Jul. 14, 2016

Related U.S. Application Data

(63) Continuation of application No. 13/858,839, filed on Apr. 8, 2013, now abandoned.

(60) Provisional application No. 61/621,454, filed on Apr. 6, 2012.

(51) Int. Cl.
*C12Q 1/6883* (2018.01)
*G16B 25/00* (2019.01)
*G16B 30/00* (2019.01)
*G16B 20/40* (2019.01)
*C12Q 1/6827* (2018.01)

(52) U.S. Cl.
CPC ......... *C12Q 1/6883* (2013.01); *C12Q 1/6827* (2013.01); *G16B 20/40* (2019.02); *G16B 25/00* (2019.02); *G16B 30/00* (2019.02); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 6,440,706 B1 | 8/2002 | Vogelstein et al. |
| 6,753,147 B2 | 6/2004 | Vogelstein et al. |
| 7,727,720 B2 | 6/2010 | Dhallan |
| 2003/0180765 A1 | 9/2003 | Traverso et al. |
| 2004/0137470 A1 | 7/2004 | Dhallan |
| 2005/0130176 A1 | 6/2005 | Vogelstein et al. |
| 2007/0202525 A1 | 8/2007 | Quake et al. |
| 2007/0207466 A1 | 9/2007 | Cantor |
| 2011/0288780 A1 | 11/2011 | Rabinowitz et al. |

FOREIGN PATENT DOCUMENTS

WO 2009/013496 A1 1/2009

OTHER PUBLICATIONS

Agarwal et al. Commercial landscape of noninvasive prenatal testing in the United States. Prenatal Diagnosis vol. 33, pp. 521-531 (Year: 2013).*
Ku et al. Exome versus transcriptome sequencing in identifying coding region variants Expert Reviews of Molecular Diagnosis vol. 12, pp. 241-251 (Year: 2012).*
Fan et al. 2010 Sensitivity of Noninvasive Prenatal Detection of Fetal Aneuploidy from Maternal Plasma Using Shotgun Sequencing Is Limited Only by Counting Statistics PLoS one vol. 5 article e10439 (Year: 2010).*
The Area Under an ROC Curve [retrieved on Apr. 22, 2019] Retrieved from the internet: http://gim.unmc.edu/dxtests/roc3.htm (Year: 2019).*
Li et al. A survey of sequence alignment algorithms for next-generation sequencing Briefings in Bioinformatics vol. 11, pp. 473-483 (Year: 2010).*
Lo et al. Maternal Plasma DNA Sequencing Reveals the Genome-Wide Genetic and Mutational Profile of the Fetus Science Translational Medicine vol. 2, pp. 1-13 (Year: 2010).*
Fan et al. 2008 Noninvasive diagnosis of fetal aneuploidy by shotgun sequencing DNA from maternal blood Proceedings of the National Academy of Sciences USA vol. 105 pp. 16266-16271 (Year: 2008).*
International Search Report and Written Opinion dated Aug. 22, 2013 in PCT/IB2013/052804, 10 pages.
Liao, G. J. W., et al., "Targeted Massively Parallel Sequencing of Maternal Plasma DNA Permits Efficient and Unbiased Detection of Fetal Alleles," Clinical Chemistry, 2011, vol. 57, No. 1, pp. 92-101.
Liao, G. J. W., et al., "Noninvasive Prenatal Diagnosis of Fetal Trisomy 21 by Allelic Ratio Analysis Using Targeted Massively Parallel Sequencing of Maternal Plasma DNA," PloS One, 2012, vol. 7, No. 5, 338154, e-pages 1-7, published online May 29, 2012.
Dhallan, R., et al., "A Non-Invasive Test for Prenatal Diagnosis Based on Fetal DNA Present in Maternal Blood: A Preliminary Study," The Lancet, 2007, vol. 369, pp. 474-481.

(Continued)

*Primary Examiner* — John S Brusca
(74) *Attorney, Agent, or Firm* — Kilpatrick Townsend & Stockton LLP

(57) ABSTRACT

Whether a fetus has an aneuploidy associated with a first chromosome is detected using ratios of alleles detected in a maternal sample having a mixture of maternal and fetal DNA. DNA from the sample is enriched for target regions associated with polymorphic loci and then sequenced. Polymorphic loci (e.g., single nucleotide polymorphisms) in the target regions with fetal-specific alleles are identified on a first chromosome and on one or more reference chromosomes. A first ratio of the fetal-specific alleles and shared alleles is determined for the loci on the first chromosome. A second ratio of the fetal-specific alleles and shared alleles is determined for the loci on the reference chromosome(s). A third ratio of the first and second ratio can be compared to a cutoff to determine whether an aneuploidy is present, and whether the aneuploidy is maternally-derived or paternally-derived.

20 Claims, 7 Drawing Sheets

(56) References Cited

OTHER PUBLICATIONS

Fan, H. C., et al., "Detection of Aneuploidy with Digital PCR," May 8, 2007, 14 pages, Department of Bioengineering, Stanford University and Howard Hughes Medical Institute, Stanford, CA.

Chang, Hsueh-Wei et al.; "Assessment of Plasma DNA Levels, Allelic Imbalance, and CA 125 as Diagnostic Tests for Cancer"; 2002, Journal of the National Cancer Institute, vol. 94, No. 22, pp. 1697-1703.

Diehl, Frank et al.; "Detection and quantification of mutations in the plasma of patients with colorectal tumors"; 2005, *PNAS*, vol. 102, No. 45, pp. 16368-16373.

El Karoui, Noureddine et al.; "Getting more from digital SNP data"; 2006, *Statistics in Medicine*, vol. 25, pp. 3124-3133.

Ottesen, Elizabeth A. et al.; "Microfluidic Digital PCR Enables Multigene Analysis of Individual Environmental Bacteria"; 2006, *Science*, vol. 314, pp. 1464-1467.

Panhard, Xaviere et al.; "Constructions of a global score quantifying allelic imbalance among biallelic SIDP markers in bladder cancer"; 2003, *Statistics in Medicine*, vol. 22, pp. 3771-3779.

Pohl, Gudrun et al.; "Principle and applications of digital PCR"; 2004, *Expert Rev. Mol. Diagn.*, vol. 4, No. 1, pp. p. 1 only.

Vogelstein, Bert et al.; "Digital PCR"; 1999, *PNAS*, vol. 96, pp. 9236-9241.

Warren, Luigi et al.; "Transcription factor profiling in individual hematopoietic progenitors by digital RT-PCR"; 2006, *PNAS*, vol. 103, No. 47, pp. 17807-17812.

Zhou, Wei et al.; "Counting alleles to predict recurrence of early-stage colorectal cancers"; 2002, *The Lancet*, vol. 359, pp. 219-225.

Chen, Eric, Z., et al., "Noninvasive Prenatal Diagnosis of Fetal Trisomy 18 and Trisomy 13 by Maternal Plasma DNA Sequencing,"PLOS One, Jul. 6, 2011, vol. 6, No. 7, 7 pages.

Chiu, Rossa, W.K., et al., "Noninvasive Prenatal Diagnosis of Fetal Chromosomal Aneuploidy by Massively Parallel Genomic Sequencing of DNA in Maternal Plasma," Proceedings of the National Academy of Sciences, Dec. 23, 2008, vol. 105, No. 51, pp. 20458-20463.

Supplementary European Search Report dated Oct. 15, 2015 in EP 13773129.5, 8 pages.

Extended European Search Report dated Mar. 30, 2017 in EP 17154021.4, 14 pages.

First Examination Report dated Oct. 27, 2017 in AU 2013245272, 3 pages.

U.S. Appl. No. 13/858,839, "Non-Final Office Action", dated Jul. 2, 2014, 10 pages.

U.S. Appl. No. 13/858,839, "Final Office Action," dated Feb. 26, 2015, 7 pages.

U.S. Appl. No. 13/858,839, "Non-Final Office Action," dated Sep. 28, 2015, 8 pages.

U.S. Appl. No. 13/858,839, "Final Office Action," dated Dec. 22, 2015, 12 pages.

JP 2015-503985, "Notice of Reasons for Rejection," dated Mar. 22, 2016, 7 pages, English translation.

CA 2,869,371, "Office Action", dated Apr. 4, 2016, 4 pages.

CA 2,869,371, "Office Action", dated Mar. 24, 2017, 4 pages.

\* cited by examiner

300

| No. | Sample name | Fetal status | Target enriched | Mapped reads[5] | Target seq depth | chr21 |  |  |  | chrRef |  |  |  | $FSR_{ref}^{21}$ |
|---|---|---|---|---|---|---|---|---|---|---|---|---|---|---|
|  |  |  |  |  |  | Info SNP | SC | FC | FSR | Info SNP | SC | FC | FSR |  |
| 1 | PW257 | euploid | No | 2 M | 0.07 | 1674 | 110 | 8 | 0.073 | 103563 | 6880 | 662 | 0.096 | 0.76 |
|  |  |  | Yes | 3.3 M | 31.18 | 268 | 7559 | 739 | 0.098 | 169 | 4951 | 377 | 0.076 | 1.29 |
| 2 | PW279 | euploid | No | 2.4 M | 0.09 | 1686 | 117 | 9 | 0.077 | 101227 | 7954 | 871 | 0.11 | 0.7 |
|  |  |  | Yes | 3.1 M | 30.3 | 289 | 7296 | 761 | 0.104 | 148 | 4129 | 449 | 0.109 | 0.95 |
| 3 | PW280 | euploid | No | 2.8 M | 0.11 | 1373 | 141 | 9 | 0.064 | 103732 | 10423 | 703 | 0.067 | 0.96 |
|  |  |  | Yes | 2.8 M | 24 | 186 | 3968 | 222 | 0.056 | 162 | 3934 | 228 | 0.058 | 0.97 |
| 4 | PW338 | euploid | No | 2.3 M | 0.09 | 1364 | 121 | 5 | 0.041 | 99581 | 8136 | 390 | 0.048 | 0.85 |
|  |  |  | Yes | 3.2 M | 28.39 | 221 | 6164 | 285 | 0.046 | 162 | 4245 | 181 | 0.043 | 1.07 |
| 5 | PW263 | euploid | No | .3 M | 0.11 | 1592 | 162 | 14 | 0.086 | 105140 | 10821 | 908 | 0.084 | 1.02 |
|  |  |  | Yes | 2.5 M | 23.35 | 253 | 5539 | 453 | 0.082 | 178 | 3770 | 301 | 0.08 | 1.03 |
| 6 | PW295 | euploid | No | 3.3 M | 0.12 | 1775 | 203 | 17 | 0.084 | 105072 | 11742 | 983 | 0.084 | 1 |
|  |  |  | Yes | 3.1 M | 30.03 | 273 | 7740 | 695 | 0.09 | 156 | 4103 | 345 | 0.084 | 1.07 |
| 7 | PW305 | euploid | No | 3.5 M | 0.13 | 1436 | 167 | 18 | 0.108 | 106341 | 12711 | 1250 | 0.098 | 1.1 |
|  |  |  | Yes | 2.4 M | 21.95 | 191 | 3610 | 343 | 0.095 | 181 | 3866 | 348 | 0.09 | 1.06 |
| 8 | PW146 | T21 | No | 2.6 M | 0.1 | 1173 | 107 | 2 | 0.019 | 106925 | 9703 | 560 | 0.058 | 0.33 |
|  |  |  | Yes | 2.1 M | 21.43 | 213 | 4536 | 197 | 0.043 | 145 | 2786 | 154 | 0.055 | 0.78 |
| 9 | PW150 | T21 | No | 2.7 M | 0.1 | 1044 | 87 | 10 | 0.115 | 106601 | 10259 | 502 | 0.049 | 2.35 |
|  |  |  | Yes | 2.8 M | 26.01 | 151 | 3878 | 250 | 0.064 | 180 | 4317 | 164 | 0.038 | 1.68 |
| 10 | PW178 | T21 | No | 2.9 M | 0.11 | 1049 | 106 | 18 | 0.17 | 106607 | 10263 | 1108 | 0.108 | 1.57 |
|  |  |  | Yes | 2.5 M | 22.83 | 169 | 3675 | 398 | 0.108 | 182 | 3610 | 331 | 0.092 | 1.17 |
| 11 | PW266 | T21 | No | 2.8 M | 0.11 | 1193 | 123 | 17 | 0.138 | 104560 | 10002 | 991 | 0.099 | 1.39 |
|  |  |  | Yes | 3 M | 29.07 | 165 | 4464 | 375 | 0.084 | 156 | 4095 | 396 | 0.097 | 0.87 |
| 12 | PW352 | T21 | No | 4.6 M | 0.17 | 1116 | 146 | 19 | 0.13 | 105157 | 16595 | 1622 | 0.098 | 1.33 |
|  |  |  | Yes | 3.5 M | 30.65 | 181 | 5153 | 483 | 0.094 | 170 | 4649 | 473 | 0.102 | 0.92 |
| 13 | PW392 | T21 | No | 3.1 M | 0.12 | 1189 | 126 | 10 | 0.079 | 105838 | 11464 | 712 | 0.062 | 1.27 |
|  |  |  | Yes | 3.5 M | 34.31 | 186 | 5934 | 325 | 0.055 | 168 | 5557 | 328 | 0.059 | 0.93 |
| 14 | PW421 | T21 | No | 5.2 M | 0.19 | 1206 | 213 | 12 | 0.056 | 106950 | 15892 | 1570 | 0.083 | 0.68 |
|  |  |  | Yes | 3.2 M | 25.45 | 192 | 4397 | 306 | 0.07 | 171 | 4231 | 305 | 0.072 | 0.97 |

FIG. 3

NONINVASIVE PRENATAL DIAGNOSIS OF FETAL TRISOMY BY ALLELIC RATIO ANALYSIS USING TARGETED MASSIVELY PARALLEL SEQUENCING

CROSS-REFERENCES TO RELATED APPLICATION

This application is a continuation application of U.S. patent application Ser. No. 13/858,839, entitled "NONINVASIVE PRENATAL DIAGNOSIS OF FETAL TRISOMY BY ALLELIC RATIO ANALYSIS USING TARGETED MASSIVELY PARALLEL SEQUENCING", filed on Apr. 8, 2013, which claims the benefit of U.S. Provisional Patent Application No. 61/621,454, entitled "NONINVASIVE PRENATAL DIAGNOSIS OF FETAL TRISOMY BY ALLELIC RATIO ANALYSIS USING TARGETED MASSIVELY PARALLEL SEQUENCING," filed on Apr. 6, 2012, the entire contents of which are herein incorporated by reference for all purposes.

BACKGROUND

Prenatal screening and diagnosis of fetal aneuploidies, such as trisomy 21 (T21), is an established part of modern obstetrics care. Conventional prenatal screening is built on parameters such as maternal age, sonographic and biochemical markers [1]. Since these parameters are mainly based on phenotypic features, which are essentially epiphenomena associated with the core molecular pathology, their diagnostic performance is usually suboptimal. Pregnancies stratified as high risk by the above screening approaches require further investigation of fetal genetic materials obtained via invasive procedures, such as chorionic villus sampling (CVS) and amniocentesis. These latter procedures carry small, but definite, risk of miscarriage [2]. The demonstration of fetal DNA in maternal plasma in 1997 has opened up possibilities for noninvasive prenatal diagnosis (NIPD) [3].

Maternal plasma DNA contains a mixture of fragmented maternal and fetal genomic DNA [4]. The large background of maternal DNA represents a challenge for the interrogation of fetal chromosomal status. Early studies for NIPD of T21 were polymorphism-based, requiring the measurements of allelic ratios and comparing them with the expected normal values [5-7]. These early methods were based on fetal-specific molecular signatures such as DNA methylation markers [5] and RNA markers [6], or required one to increase the fractional fetal DNA concentration to a sufficiently high level such as using formaldehyde treatment of maternal plasma [7]. However, for the last approach, there are controversies on the effectiveness of formaldehyde treatment because this method could not be replicated consistently by different groups [8-10]. Therefore, the clinical applicability of such a method remains unclear.

It is therefore desirable to provide new techniques for noninvasive prenatal diagnosis using allelic ratios.

BRIEF SUMMARY

Embodiments provide methods, apparatuses, and systems for non-invasively determining whether a fetus has an aneuploidy associated with a first chromosome by analyzing a biological sample containing a mixture of cell-free fetal and maternal DNA. For example, a first allelic ratio can be determined for the first chromosome and a second allelic ratio can be determined for one or more reference chromosomes. To determine the ratios, DNA can be enriched for target regions associated with polymorphic loci and then sequenced. Loci in the target regions with fetal-specific alleles are identified on a first chromosome and on one or more reference chromosomes. These loci can be used to determine respective allelic ratios. A third ratio of the first and second allelic ratios can be compared to a cutoff to determine whether an aneuploidy is present for the first chromosome, and whether the aneuploidy is maternally-derived or paternally-derived.

Other embodiments are directed to systems, portable consumer devices, and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 3 shows a table of sequencing results of 14 pregnant women according to embodiments of the present invention.

DEFINITIONS

Figures 1A, 1B, 1C:
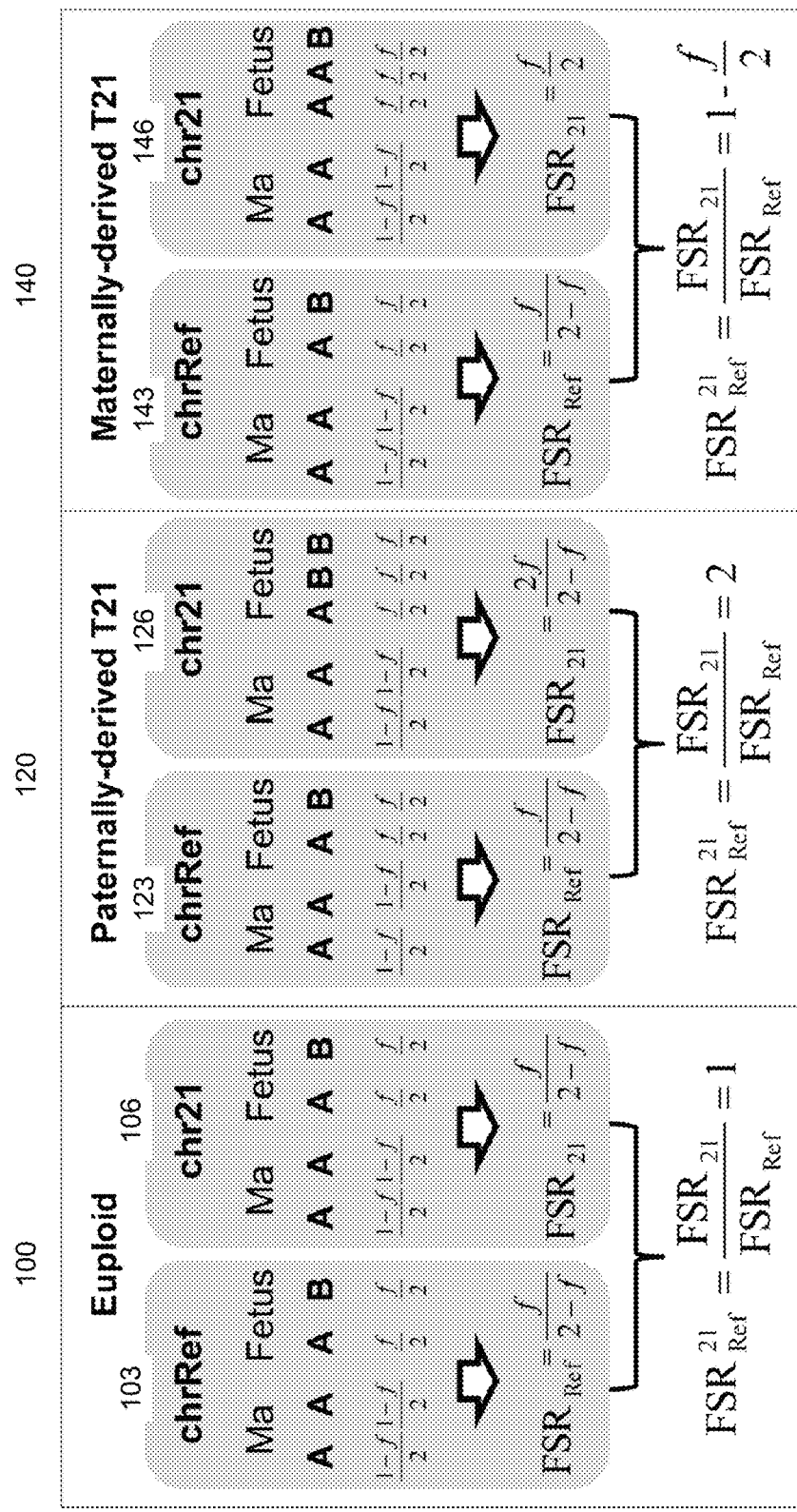
FIG. 1A shows a diagram 100 of alleles at a locus for the mother and a euploid fetus and an example calculation according to embodiments of the present invention.
FIG. 1B shows a diagram 120 of alleles at a locus for the mother and a paternally-derived aneuploid fetus and an example calculation according to embodiments of the present invention.
FIG. 1C shows a diagram 140 of alleles at a locus for the mother and a maternally-derived aneuploid fetus and an example calculation according to embodiments of the present invention.

The term "biological sample" as used herein refers to any sample that is taken from a subject (e.g., a human, such as a pregnant woman) and contains one or more nucleic acid molecule(s) of interest. Examples include plasma, saliva, pleural fluid, sweath, ascitic fluid, bile, urine, serum, pancreatic juice, stool and cervical smear samples The term "nucleic acid" or "polynucleotide" refers to a deoxyribonucleic acid (DNA) or ribonucleic acid (RNA) and a polymer thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer M A et al., *Nucleic Acid Res* 1991; 19:5081; Ohtsuka E et al., *J Biol Chem* 1985; 260:2605-2608; and Rossolini G M et al., *Mol Cell Probes* 1994; 8:91-98). The term nucleic acid is used interchangeably with gene, cDNA, mRNA, small non-coding RNA, micro RNA (miRNA), Piwi-interacting RNA, and short hairpin RNA (shRNA) encoded by a gene or locus.

The term "gene" means the segment of DNA involved in producing a polypeptide chain. It may include regions preceding and following the coding region (leader and trailer) as well as intervening sequences (introns) between individual coding segments (exons).

As used herein, the term "locus" or its plural form "loci" is a location or address of any length of nucleotides (or base pairs) which has a variation across genomes. A SNP is informative if it is homozygous in the mother (e.g., genotype AA) and heterozygous in the fetus (e.g., genotype AB).

The term "sequenced tag" (also called sequence read) refers to a sequence obtained from all or part of a nucleic acid molecule, e.g., a DNA fragment. In one embodiment, just one end of the fragment is sequenced, e.g., about 30 bp. The sequenced tag can then be aligned to a reference genome. Alternatively, both ends of the fragment can be sequenced to generate two sequenced tags, which can provide greater accuracy in the alignment and also provide a length of the fragment. In yet another embodiment, a linear DNA fragment can be circularized, e.g., by ligation, and the part spanning the ligation site can be sequenced.

The term "universal sequencing" refers to sequencing where adapters are added to the end of a fragment, and the primers for sequencing attached to the adapters. Thus, any fragment can be sequenced with the same primer, and thus the sequencing can be random.

The term fractional fetal DNA concentration is used interchangeably with the terms fetal DNA proportion and fetal DNA fraction, and refers to the proportion of DNA molecules that are present in a maternal plasma or serum sample that is derived from the fetus (Lo Y M D et al. *Am J Hum Genet* 1998; 62:768-775; Lun F M F et al. *Clin Chem* 2008; 54:1664-1672).

The term "overrepresented nucleic acid sequence" as used herein refers to the nucleic acid sequence among two sequences of interest (e.g., a clinically relevant sequence and a background sequence) that is in more abundance than the other sequence in a biological sample. For example, the maternal (shared allele) would be overrepresented at an informative locus.

The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter.

The term "cutoff value" as used herein means a numerical value whose value is used to arbitrate between two or more states (e.g. diseased and non-diseased) of classification for a biological sample. For example, if a parameter is greater than the cutoff value, a first classification of the quantitative data is made (e.g. diseased state); or if the parameter is less than the cutoff value, a different classification of the quantitative data is made (e.g. non-diseased state).

The term "chromosomal aneuploidy" as used herein means a variation in the quantitative amount of a chromosome from that of a diploid genome. The variation may be a gain or a loss. It may involve the whole of one chromosome or a region of a chromosome.

Nonstandard abbreviations are: NIPD, noninvasive prenatal diagnosis; MPS, massively parallel sequencing; chr21, chromosome 21; chrRef, reference chromosome; T21, trisomy 21; SNP, single nucleotide polymorphism; FSR, F-S ratio, ratio between the fetus-specific allele and the shared allele; FC, fetus-specific allelic counts; and SC, shared allelic counts.

DETAILED DESCRIPTION

Plasma DNA obtained from a pregnant woman contains a mixture of cell-free maternal and cell-free fetal DNA. The fetal DNA proportion in maternal plasma is relatively consistent as determined using polymorphic genetic markers across different chromosomes in euploid pregnancies. For example, the proportion of counts of a first fetal-specific allele at a first locus is relatively consistent with the proportion counts of a second fetal-specific allele at any other locus. The fetal DNA proportion may differ from one maternal sample to another, but the fetal DNA proportion for different polymorphic genetic markers (on the same chromosome or different chromosomes) is relatively consistent within the sample.

For aneuploid pregnancies, the observed fetal DNA proportion measured using polymorphic genetic markers for the aneuploid chromosome would be perturbed. Embodiments use polymorphisms (e.g., single nucleotide polymorphisms) with fetus-specific alleles to detect such perturbations in mothers carrying aneuploidy fetuses (e.g., trisomy 21 fetuses). Although the percentage of fetal DNA is typically less than the percentage of maternal DNA, the fetal DNA percentage is typically high enough to identify the perturbation. But, the fetal DNA proportion may differ from one sample to another, thereby adding some complexity to the identification of the complexity.

To address this complexity, embodiments can determine a ratio using a first fetal DNA proportion from polymorphic genetic markers for the aneuploid chromosome and a second fetal DNA proportion for reference chromosomes not involved in the aneuploidy. The fetal DNA proportion for polymorphic genetic markers on the reference chromosomes would not be perturbed by the aneuploidy. Using such a second proportion determined from genetic markers on the reference chromosomes can provide an accurate parameter (e.g., the ratio of the two proportions) for identifying an aneuploidy, particularly when specific parts of the genome are enriched for known polymorphic sites. Such enrichment can provide greater efficiency by increasing the number of analyzed DNA molecules that correspond to usable polymorphic markers, relative to other DNA molecules that are not used in determining the parameter.

I. Introduction

An approach for NIPD of aneuploidies (such as T21) is to measure the proportion of chromosome 21 (chr21)-derived DNA molecules in a maternal plasma sample. If a mother is carrying a T21 fetus, the additional copy of chr21 from the fetus would contribute an additional amount of chr21 DNA molecules to the maternal plasma sample, leading to an increased proportion of chr21 sequences [11]. Massively parallel sequencing (MPS) enhances the precision of DNA quantification, and has enabled the detection of aberrant quantities of fetal DNA derived from an aneuploid chromosome [11-14].

Embodiments use an allelic ratio approach for the NIPD of an aneuploidy (such as T21) by using MPS. Since single nucleotide polymorphisms (SNPs) only account for approximately 1.6% of the human genome according to the dbSNP Build 135 for human (www.ncbi.nlm.nih.gov/projects/SNP/), conventional non-targeted MPS would only include SNP alleles in a small proportion of sequence reads. Therefore, embodiments can use targeted MPS to preferentially sequence selected SNP loci in a biological sample (e.g., maternal plasma) for fetal aneuploid detection. In a previous publication, by using a hybridization-based targeted MPS platform, the inventors demonstrated the enrichment of DNA molecules within the targeted regions, as well as the preservation of the allelic ratios of the targeted SNPs in maternal plasma after target enrichment [15].

A SNP (or other polymorphism) is informative if it is homozygous in the mother (e.g., genotype AA) and heterozygous in the fetus (e.g., genotype AB). In this scenario, the B allele is the fetus-specific allele and the A allele is the allele shared by the mother and fetus. The fetus-specific allelic counts and shared allelic counts for the informative SNPs can be obtained from sequencing plasma DNA, and used to calculate a ratio between the count fetus-specific alleles and the shared alleles. An example of the ratio is labeled FSR.

In one implementation where the chromosome of interest is chromosome 21, the ratio can be expressed as F-S ratio for chr21 (expressed as $FSR_{21}$) and the reference chromosomes (expressed as $FSR_{Ref}$). If a mother is carrying a euploid fetus, the ratio between $FSR_{21}$ and $FSR_{Ref}$ (expressed as $FSR_{Ref}^{21}$) should be equal to 1 (FIG. 1A). If a mother is carrying a T21 fetus with an additional chr21 from the father (referred in this manuscript as paternally-derived T21), the fetal genotype on chr21 would become ABB. The additional copy of the fetus-specific allele would increase the $FSR_{Ref}^{21}$ to 2 (FIG. 1B). If the extra copy of chr21 is from the mother (referred in this manuscript as maternally-derived T21), the fetal genotype on chr21 would become AAB. The additional copy of the shared allele would reduce the $FSR_{Ref}^{21}$ to less than 1 (FIG. 1).

A. Euploid

FIG. 1A shows a diagram 100 of alleles at a locus for the mother and a euploid fetus and an example calculation according to embodiments of the present invention. Locus 103 is for a reference chromosome and locus 106 is for chromosome 21 (but it could be any chromosome of interest). The maternal genome is homozygous at each locus and the fetus is heterozygous at each locus. As depicted, the maternal allele is labeled A at each locus, although the actual sequence for the two loci would be different. Thus, A and B are simply labels highlighting two different alleles at a same locus (i.e., alleles from two different copies of the chromosome), and in this case two alleles in the fetal genome.

The paternal allele B is inherited by the fetus from the father, thereby making the fetus heterozygous at the two loci. Other similarly situated loci (informative loci) can be found on the reference chromosome and the chromosome of interest. Thus, locus 103 can actually be loci 103, and locus 106 can be loci 106. There can also be more than one reference chromosome.

For the euploid case, the fetus has one allele A and one allele B at loci 103 and loci 106. In an example where the fetal DNA percentage is 50% (i.e., equal parts maternal and fetal DNA), there would be 25% proportion of paternal alleles B detected at loci 103 and 25% proportion of paternal alleles B at loci 106. Therefore, a ratio of the two proportions (i.e., 25% divided by 25%) would be one. Similarly, a ratio of B alleles to A alleles is ⅓ for loci 103 and 106, and ⅓ divided by ⅓ would be one. Of course, due to statistical nature of the sample set of detected alleles, the ratio would probably not be exactly one. Thus, a proportion (e.g., any ratio of counts of the alleles) of paternal alleles B at locus 103 should be the same as the proportion of paternal alleles B.

FIG. 1A provides a more general formulation for different fractional fetal DNA concentrations f. As shown, at each locus 103, the fetus would contribute a proportion of f/2 of allele B out of all of the alleles detected at locus 103. As mentioned above, if f was 0.5, then the proportion would be 0.25, or 25%. Similarly, the fetus would contribute f/2 of allele A. The higher the fractional fetal DNA concentration, the higher the proportion of allele B would be. Here, f is defined as DNA of either genotype of the fetus, and thus the factor of two.

For the mother, each copy of the chromosome contributes the same proportion (1−f)/2. When f is 0.5, the proportion is 0.25 (25%) as noted above. In the limit of 0% fetal DNA, each allele A contributes 50%, and only the A sequence is detected as the mother is homozygous.

The ratio of B alleles relative to A alleles detected at each locus 103 and 106 is given as f/(2−f). For example, if f is 0.5, then the ratio is ⅓, since there is one B allele for each A allele. Other ratios may be used, e.g., the percentage of paternal alleles B detected for all loci 103, as given by B/(A+B) or 2B/(A+B), where A and B here are the counts of the corresponding alleles. The ratio shown is labeled FSR, as the ratio of the count of fetal-specific (paternal) allele and the shared (maternal) allele.

B. Paternally-Derived Aneuploidy

FIG. 1B shows a diagram 120 of alleles at a locus for the mother and a paternally-derived aneuploid fetus and an example calculation according to embodiments of the present invention. Locus 123 is for a reference chromosome and locus 126 is for chromosome 21. As for FIG. 1A, the maternal genome is homozygous at each locus and the fetus is heterozygous at each locus.

For this aneuploid case, the fetus has one allele A and one allele B at loci 123, but has one allele A and two allele B at loci 126, as there is an extra copy of chromosome 21 from the father. In an example where the fetal DNA percentage is 50% (i.e., equal parts maternal and fetal DNA), the ratio of B alleles to A alleles for loci 123 would ⅓, but would be ⅔ for loci 126 since there is two B alleles.

For the general formula, each copy of the chromosome can be considered to contribute f/2, since the fetal concentration is determined with respect to the reference chromosome(s). Thus, the sum of the counts of allele B provides f/2+f/2=f. The sum of counts of allele A provides f/2+1−f. The ratio of these provides 2f/(2−f), as shown. The ratio $FSR_{Ref}$ for the reference chromosome is still the same as for FIG. 1A, since this chromosome is still euploid.

The ratio of the ratio $FSR_{21}$ and $FSR_{Ref}$ is two. Of course, due to statistical nature of the sample set of detected alleles, the ratio would probably not be exactly two. The paternally-derived aneuploidy is easier to detect that the maternally-derived aneuploidy as described below.

C. Maternally-Derived Aneuploidy

FIG. 1C shows a diagram 140 of alleles at a locus for the mother and a maternally-derived aneuploid fetus and an example calculation according to embodiments of the present invention. Locus 143 is for a reference chromosome and locus 146 is for chromosome 21. As for FIG. 1A, the maternal genome is homozygous at each locus and the fetus is heterozygous at each locus.

For this aneuploid case, the fetus has one allele A and one allele B at loci 143, but has two allele A and one allele B at loci 146, as there is an extra copy of chromosome 21 from the mother. In an example where the fetal DNA percentage is 50% (i.e., equal parts maternal and fetal DNA), the ratio of B alleles to A alleles for loci 143 would ⅓, but would be ¼ for loci 146 since there is one allele B for every 1 allele A.

For the general formula, each copy of the chromosome can be considered to contribute f/2, since the fetal concentration is determined with respect to the reference chromosome(s). Thus, the sum of the counts of allele B provides f/2. The sum of counts of allele A provides 1−f+f/2+f/2, which gives simply 1. The ratio of these provides f/2, as shown. The ratio $FSR_{Ref}$ for the reference chromosome is still the same as for FIG. 1A, since this chromosome is still euploid. The ratio of the ratio $FSR_{21}$ and $FSR_{Ref}$ is 1−f/2. Of course, due to statistical nature of the sample set of detected alleles, the ratio would probably not be exactly 1−f/2.

To determine which of these categories a sample corresponds to, the final ration can be compared to a cutoff value. For example, a cutoff somewhere between 1 and 2 can distinguish the euploid case with the paternally-derived aneuploidy case. More than one cutoff value could be used between 1 and 2, thereby providing different levels of confidence for a determination. The cutoff value between the euploid and the maternally-derived aneuploidy is more difficult as the spacing between the two values is smaller, and depends on the fraction fetal concentration f. The cutoff could be determined from a separate measurement off to determine an expected value if the fetus at a maternally-derived aneuploidy. As another example, a minimum value off could be required, and then a same cutoff value suitable for that minimum fetal concentration could be used.

Accordingly, for the example of T21, assuming the fractional fetal DNA concentration in chrRef is f, the F-S ratio would be f/(2−f) on chrRef irrespective of the aneuploidy status of the fetus. On the other hand, the F-S ratio on chr21 would be f/(2−f) if the mother is carrying a euploid fetus, 2f/(2−f) if the mother is carrying a paternally-derived T21 fetus, and f/2 if the mother is carrying a maternally-derived T21 fetus. Therefore, the $FSR_{Ref}^{21}$ would be 1 if the mother is carrying a euploid fetus, would become 2 if the mother is carrying a paternally-derived T21 fetus, and would become (1−f/2) if the mother is carrying a maternally-derived T21 fetus.

II. Method

Figure 2:
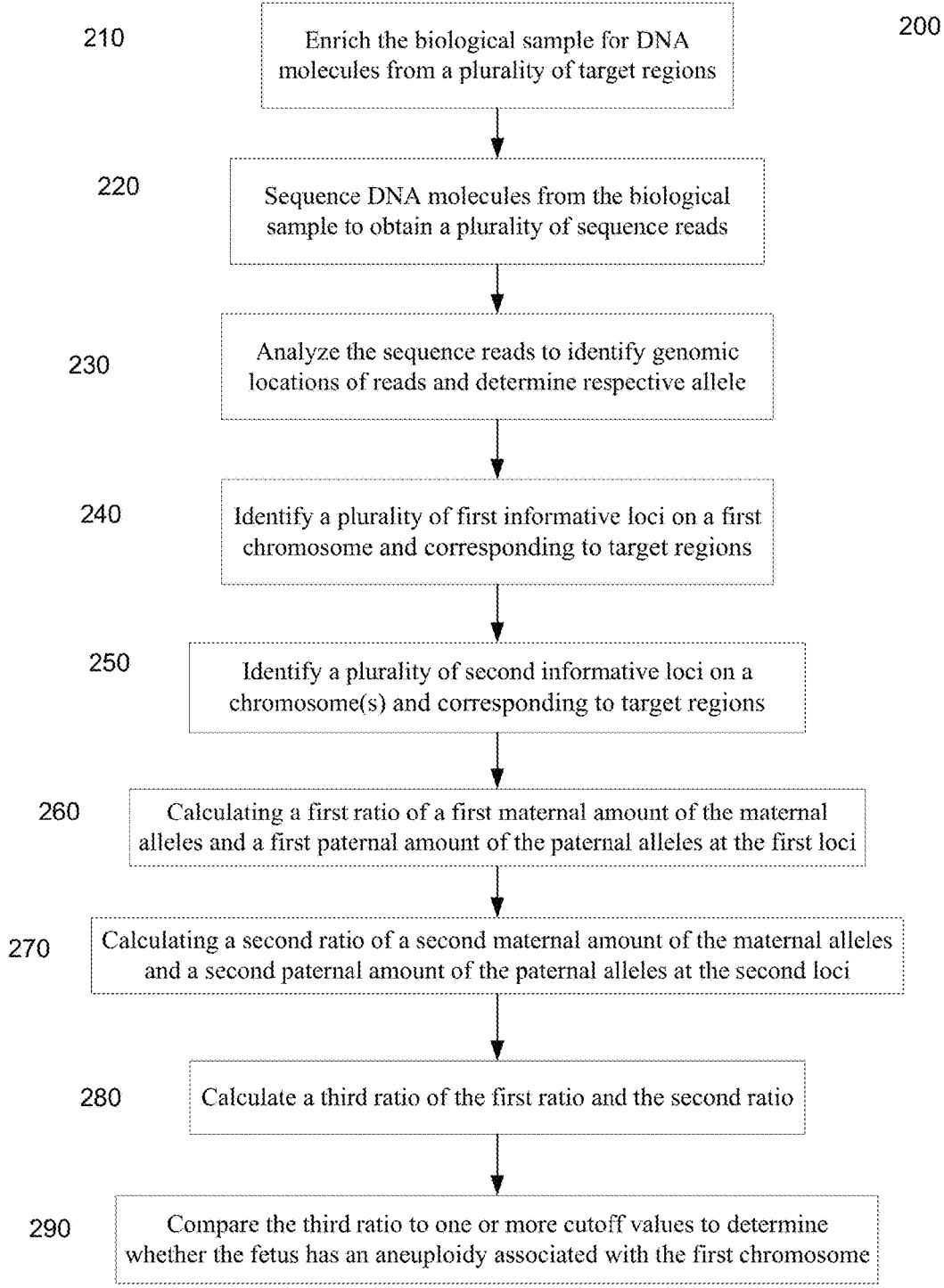
FIG. 2 is a flowchart illustrating a method 200 of analyzing a biological sample from a female subject pregnant with a fetus to determine whether the fetus has an aneuploidy.

FIG. 2 is a flowchart illustrating a method 200 of analyzing a biological sample from a female subject pregnant with a fetus to determine whether the fetus has an aneuploidy. The biological sample contains a mixture of DNA molecules from the fetus and the female subject. Parts of method 200 may be performed by a computer system.

At block 210, the biological sample is enriched for DNA molecules from a plurality of target regions. The enrichment can be performed by hybridization techniques or amplification techniques, or a combination of both. The target regions can be genomic regions that are known to have polymorphic sites. Such regions can include those of the Genome-Wide Human SNP Array 6.0 (Affymetrix).

At block 220, DNA molecules from the biological sample are sequenced to obtain a plurality of sequence reads. The sequencing may be performed in a variety of ways. For example, a universal sequencing can use the same adapters ligated to the end of the molecules for sequencing any DNA molecule. One embodiment uses massively parallel DNA sequencing, such as, but not limited to that performed by the Illumina Genome Analyzer platform (Bentley D R et al. Nature 2008; 456: 53-59), the Roche 454 platform (Margulies M et al. Nature 2005; 437: 376-380), the ABI SOLiD platform (McKernan K J et al. Genome Res 2009; 19: 1527-1541), the Helicos single molecule sequencing platform (Harris T D et al. Science 2008; 320: 106-109), real-time sequencing using single polymerase molecules (Science 2009; 323: 133-138) and nanopore sequencing (Clarke J et al. Nat Nanotechnol. 2009; 4: 265-70). In one implementation, the sequencing is paired-end sequencing that provides a pair of reads for each DNA molecule sequenced.

At block 230, the plurality of sequence reads are analyzed. The analyzing a sequence read can include identifying a location of the sequence read in a reference genome by aligning the sequence read to the reference genome, and determining a respective allele of the sequence read. The respective allele is determined from the sequence of the read. For a heterozygous locus, the sequence read can inform which allele corresponds to the sequence read. The reference genome can include locations where polymorphisms are known to exist and allow alignment for either allele.

At block 240, a plurality of first loci on a first chromosome are identified, where the plurality of first loci correspond to a portion of the target regions. The first loci are informative in that the mother is homozygous at the loci and the fetus is heterozygous. These loci can be determined from the sequencing reads when reads having two different alleles align to the same location in the reference genome, and where one allele is in a significant majority. Since the fetal concentration is expected to be between 5%-20%, informative loci might be expected to have a minority allele appearing about 2.5%-10%. These percentages are illustrative and other percentages may be used. Such first loci that are within a target region (i.e., a region that was enriched) can be identified for further analysis.

At block 250, a plurality of second loci on one or more reference chromosomes are identified, where the plurality of second loci correspond to a portion of the target regions. The pregnant female is homozygous for a respective maternal allele at each of the first and second loci, and the fetus is heterozygous for the respective maternal allele and a respective paternal allele at each of the first and second loci. The paternal allele is the fetal-specific allele, and thus the respective paternal alleles being different from the respective maternal alleles.

At block 260, a first ratio of a first maternal amount and a first paternal amount is calculated. The first maternal amount is of the respective maternal alleles at the plurality of first loci. For example, the number of maternal alleles counted at each first loci may be counted. The first paternal amount is of the respective paternal alleles at the plurality of first loci. As described above, the ratio can be strict division of the two amounts, with either in the denominator, but can also be other ratios, e.g., where the denominator includes a sum of the two values.

At block 270, a second ratio of a second maternal amount and a second paternal amount is calculated. The second maternal amount is of the respective maternal alleles at the plurality of second loci. The second paternal amount is of the respective paternal alleles at the plurality of second loci. The second ratio should have the same form as the first ratio, and the formula for determining the ratios should be the same. For example, sum alleles B divided by sum of alleles A.

At block 280, a third ratio of the first ratio and the second ratio is calculated. The third ratio can also be a simple ratio with either the first ratio of the second ratio being in the denominator. The ratio can also involve sums in the denominator or numerator, as well as be a ratio of functions of the first and second ratios, as can still convey a relative value between the first and second ratio.

At block 290, the third ratio is compared to one or more cutoff values to determine whether the fetus has an aneuploidy associated with the first chromosome. More than one cutoff can be used, e.g., to differentiate between the euploid, the maternally-derived aneuploidy, and the paternally-derived aneuploidy. The cutoff values can be derived in a variety of ways. For example, distributions among test samples whose results are known can be used to determine the statistical distribution of the third ratio (e.g., $FSR_{Ref}^{21}$) for each of the cases and a cutoff value can be chosen to accurately differentiate new cases that would fall within the known distributions. Theoretical values could also be used, e.g., based on expected distributions.

The cutoff values can be determined as outlined in FIGS. 1A-1C. For example, the cutoff value can differentiate when the third ratio is approximately two, and thus determine that the aneuploidy is paternally-derived. The determination of approximately being two can be made by the third ratio being above a cutoff meant to distinguish a value of 1 and a value of 2. As another example, the cutoff value can differentiate when the third ratio is approximately 1−f/2, and thus determine that the aneuploidy is maternally-derived, where f is a fractional fetal DNA concentration in the mixture. The fractional fetal DNA concentration f may be determined from the second paternal amount and the second maternal amount. For example, the following formula can be used fractional fetal DNA concentration=second paternal amount×2/(second paternal amount+second maternal amount)×100%. The cutoff value can be placed at an appropriate value between 1 and 1−f/2 to differentiate between the two cases.

III. Enriching

The enriching can be performed by selectively amplifying and/or capturing targeted regions from a DNA sample before sequencing. The enrichment is effected by probes and/or primers that are designed to hybridize to a particular location in the genome. Many of these probes/primers may be used to target multiple regions of the genome. Various regions can be targeted on the chromosome of interest and various regions can be targeted on one reference chromosome or across multiple reference chromosomes.

In one implementation, the target regions include regions that are known to have polymorphisms. In this way, one does need to know the specific polymorphisms of the fetus ahead of time. But, since the target regions correspond to polymorphisms generally found in a population, there is a good chance that the father passed one of those polymorphisms to the fetus. The mother and father could also be genotyped, thereby allowing specific knowledge of polymorphic sites of the fetus, as is described herein.

A. Capture

A rationale of capture (e.g., using an array) is to hybridize a DNA library to immobilized probes. For example, the probes correspond to a target region, and DNA molecules from these target regions hybridized to the immobilized probes. Thus, the targeted DNA is immobilized, while the non-targeted DNA is not.

Non-targeted DNA fragments can be removed by washing, and targeted fragments are can be harvested by elution. A vast excess of DNA in the library (20 g per sample) over that of the probes may be required to ensure complete hybridization. Example techniques include on-array capture (20) and in-solution capture (21). In some embodiments, probes may be designed for SNP loci that are known to show high polymorphic rate in the population. Only the SNP loci that turn out to be informative would be used for the calculation. Such an approach is generally easier to execute in a clinical setting that an approach that requires custom selection of probes for every pregnancy, e.g., when a specific sited for a fetal-specific allele is known, as may be done by identifying sites where the mother and father are homozygous for different alleles.

The capturing may not be perfect, as some DNA molecules from non-target regions may remain, the percentage of DNA molecules from target regions increased relative to the percentage before enrichment. In this manner, there is a higher likelihood that a sequence read corresponds to a target region. Therefore, less sequencing needs to be performed to get a same number of allelic counts for the various loci.

B. Amplification

For amplification, primers are designed to amplify target regions of the genome. Whereas, capture techniques remove DNA from non-targeted regions, amplification techniques preferentially increase the number of DNA molecules from the target regions. In this manner, there again is a higher likelihood that a sequence read corresponds to a target region.

Amplification can provide many copies of DNA from the target regions for sequencing, but the overall accuracy is still related to the statistical accuracy of the original sample. That is, if the original sample is relatively small (and thus susceptible to statistical inaccuracies due to the sample size), the amplification will not overcome such issues, even though more copies of DNA now exist.

In one embodiment, may combine the two techniques. For example, one may capture DNA molecules for a target region, and remove non-target DNA. The remaining DNA have an increased percentage from the target regions. One can then amplify the remaining DNA molecules to increase the target percentage even higher, and to get more copies of DNA from the target regions.

IV. Identifying Loci

As described above, embodiments use informative loci, where the mother is homozygous and the fetus is heterozygous. These loci can be identified in various ways. For example, informative loci (e.g., SNPs) may be identified according to maternal and fetal genotyping information. However, such a process would involve obtaining fetal cells, e.g., from an invasive technique. For example, the genotyping can be done on the maternal blood cells and a fetal tissue sample obtained invasively. Other embodiments can identify the informative loci from noninvasive techniques. But, this genotyping can be used as a gold standard to compare the validity of noninvasive methods. For the non-targeted sequencing results below, the read depth was not high enough to identify many informative loci based on the sequencing alone, and thus prior genotyping information regarding the informative loci was used.

For targeted sequencing embodiments, there is enough depth at more SNP loci where one can identify the presence of two alleles but one at a lower amount, and these are the likely informative loci. For example, for a locus, one can count a first number of sequence reads corresponding to a first allele and count a second number of sequence reads corresponding to a second allele. The overrepresented sequence (allele) would correspond to the shared allele and the underrepresented allele would correspond to the fetal-specific allele. Loci where the mother is heterozygous (i.e., about 50-50 of the two alleles) can be distinguished by dismissing loci where the ratio of the two alleles is about one. Since the fetal concentration is expected to be between 5%-20%, informative loci might be expected to have a minority allele appearing about 2.5%-10% out of all sequence reads aligning to the locus. These percentages are illustrative and other percentages may be used.

In one embodiment, a first number of sequence reads corresponding to the first allele at the first locus can be determined. A second number of sequence reads corresponding to the second allele at the first locus can be determined. An allelic ratio of the first number and the second number may be calculated in a variety of ways (e.g., as percentage of reads with the first allele). If the allelic ratio is above a first threshold and below a second threshold, the first locus can be identified as an informative locus. For example, the second threshold can be used to ensure that the locus is not simply heterozygous in the mother and the first threshold could be 0 (or some other value to ensure that the sequence read was simply not in error).

V. Results

DNA was extracted from plasma samples collected from fourteen pregnant women carrying singleton fetuses. Hybridization-based targeted sequencing was used to enrich 2,906 single nucleotide polymorphism loci on chr7, chr13, chr18 and chr21. Plasma DNA libraries with and without target enrichment were analyzed by massively parallel sequencing. Genomic DNA samples of both the mother and fetus for each case were genotyped by single nucleotide polymorphism microarray analysis.

FIG. 3 shows a table 300 of sequencing results of 14 pregnant women according to embodiments of the present invention. Table 300 shows data where chromosome 21 is the chromosome of interest. The fetal status was determined from the genotyping data. The rest of the data is determined from the sequencing results.

For the targeted regions, the mean sequencing depth of the enriched samples was 225-fold higher than that of the non-enriched samples. Sequencing depth can be defined as the mean number of times each base had been sequenced in a particular region. On average, 3 million paired-end reads in non-enriched and enriched samples were mapped uniquely to the reference human genome (Hg18). After filtration of the duplicated paired-end reads, the sequencing depth of the targeted region can be calculated by dividing the total number of sequenced bases within the targeted region by the length of the targeted region. The mean sequencing depth was 0.12 time for the non-enriched samples and 27 times for the enriched samples, indicating a mean enrichment of 225-fold. This finding was consistent with our previous publication [15].

The fractional fetal DNA concentrations (also referred to as the fetal DNA percentage) in the non-enriched samples was calculated by using the informative SNPs from all autosomes except for chr21, according to the equation: fractional fetal DNA concentration=fetus-specific allelic counts×2/(fetus-specific allelic counts+shared allelic counts)×100%. The median fractional fetal DNA concentration for the fourteen cases analyzed in this study was 15.5% (range 9.1%-19.7%). The fractional fetal DNA concentration can be used to determine the expected reduction in the third ratio of method 200 (e.g., $FSR_{Ref}^{21}$) from a value of 1 for maternally-derived aneuploidies (FIG. 1C). As mentioned herein, a cutoff value can be determined based on the fractional fetal DNA concentration. Alternatively, a cutoff can be chosen based on an assumption or measurement that a minimum fractional fetal DNA concentration exists in the sample.

A. F-S Ratio Calculation Using Non-Targeted Sequencing Data

Figure 4:
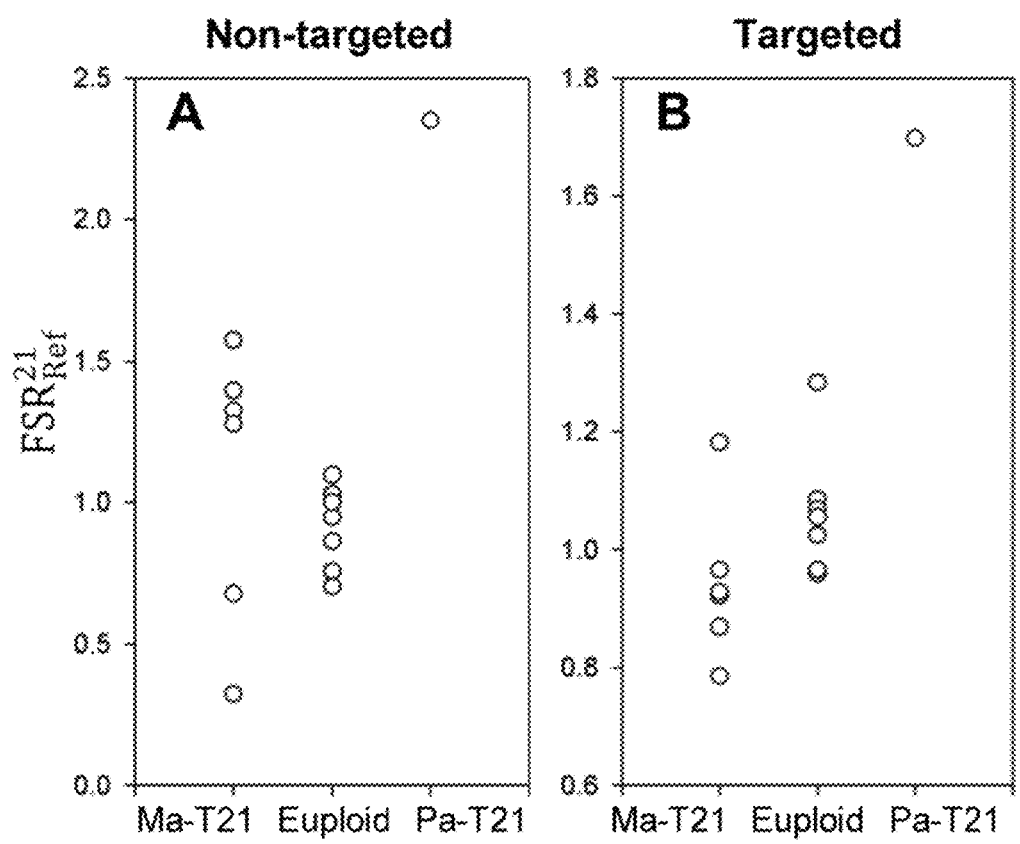
FIG. 4 shows T21 detection by F-S ratio in non-targeted and targeted sequencing data. $FSR_{Ref}^{21}$ values were calculated to differentiate the paternally- and maternally-derived T21 from the euploid fetuses in non-targeted (A) and targeted (B) sequencing data. (Ma-T21: maternally-derived T21. Pa-T21: paternally-derived T21.)

FIG. 4A shows $FSR_{Ref}^{21}$ values were calculated to differentiate the paternally- and maternally-derived T21 from the euploid fetuses from the non-targeted sequencing data according to embodiments of the present invention. Based on maternal and fetal genotyping information, informative SNPs were identified on chr21 (range amongst the samples: 1,044 to 1 775 SNPs), and chrRef which included all autosomes except chr21 (range amongst the samples: 99,581 to 106,950 SNPs). Within the above informative SNPs, fetus-specific allelic counts (expressed as FC) and shared allelic counts (expressed as SC) were determined for chr21 ($FC_{21}$=2 to 19, $SC_{21}$=87 to 213) and chrRef ($FC_{Ref}$=390 to 1,622, $SC_{Ref}$=6,880 to 18,892). FIG. 3 shows the results calculated for $FSR_{21}$, $FSR_{Ref}$ and $FSR_{Ref}^{21}$ As shown in FIG. 4A, the paternally-derived T21 case ($FSR_{Ref}^{21}$=2.35) could be differentiated from the euploid group ($FSR_{Ref}^{21}$ mean 0.91, median 0.96, range 0.70 to 1.10). On the other hand, the maternally-derived T21 cases ($FSR_{Ref}^{21}$ mean 1.10, median 1.30, range 0.33 to 1.57) overlapped with the euploid cases (Mann-Whitney rank sum test, p=0.366).

B. F-S Ratio Calculation Using Targeted Sequencing Data

FIG. 4B shows $FSR_{Ref}^{21}$ values were calculated to differentiate the paternally- and maternally-derived T21 from the euploid fetuses from the non-targeted sequencing data according to embodiments of the present invention. Among the 1,437 targeted SNP loci on chr21 and 1,469 SNP loci on chrRef (including chr7, chr13 and chr18), informative SNPs (chr21=151 to 273 SNPs, chrRef=145 to 182 SNPs) were identified for each case. The number of sequenced reads with the fetus-specific and shared alleles were determined for chr21 ($FC_{21}$=197 to 761, $SC_{21}$=3 610 to 7,740) and chrRef ($FC_{Ref}$=154 to 473, $SC_{Ref}$=2,786 to 5,557), as shown in table 300.

As shown in FIG. 4B, the paternally-derived T21 case ($FSR_{Ref}^{21}$=1.68) could be differentiated from the euploid group ($FSR_{Ref}^{21}$ mean 1.06, median 1.06, range 0.95 to 1.29). Although the maternally-derived T21 group had lower $FSR_{Ref}^{21}$ values ($FSR_{Ref}^{21}$ mean 0.94, median 0.93, range 0.78 to 1.17) (Mann-Whitney rank sum test, p=0.051), there was still overlap with the euploid group. However, the overlap decreased. The existence of the overlap suggests that the number of loci should be increased and/or the level of sequencing depth increased.

C. Comparison

The paternally-derived T21 case was successfully detected in both non-targeted and targeted sequencing data. For the maternally-derived T21 cases, this approach became less effective. Although the mean $FSR_{Ref}^{21}$ values was lower in the maternally-derived T21 cases, there was significant overlapping in the $FSR_{Ref}^{21}$ values between the euploid and the maternally-derived T21 cases. The difference in performances between paternally- and maternally-derived T21 detection was mainly due to the magnitude of the change in $FSR_{Ref}^{21}$, which was increased by 2-fold for paternally-derived T21 and decreased by f/2-fold for maternally-derived T21 (FIGS. 1B and 1C). Thus, the paternally inherited aneuploidy could be distinguished noninvasively at lower sequencing depth than maternally-inherited aneuploidy.

Since the fetal DNA represents a minor population in maternal plasma, the lower fractional concentration of fetal DNA would diminish the degree of $FSR_{Ref}^{21}$ change in maternally-derived T21. For example, assuming the fractional fetal DNA concentration is 5%, the $FSR_{Ref}^{21}$ of maternally-derived T21 would become 0.975, which is very close to that of a euploid case ($FSR_{Ref}^{21}=1$).

VI. Computer Simulation

Computer simulation was employed to investigate the accuracy of the F-S ratio analysis for T21 detection. The statistical model is based on the assumption that the numbers of fetus-specific and shared allelic counts should follow a binomial distribution, according to the fractional fetal DNA concentration in both the paternally- and maternally-derived T21 models. For example, assuming the fractional fetal DNA concentration in the reference chromosomes (chrRef) is f, the probability of detecting the fetus-specific allele for an informative SNP would be f/2 on chrRef irrespective of the aneuploidy status of the fetus. On the other hand, the probability of detecting the fetus-specific allele on chr21 would be f/2 if the mother is carrying a euploid fetus, 2f/(2+f) if the mother is carrying a paternally-derived T21 fetus, and f/(2+f) if the mother is carrying a maternally-derived T21 fetus (FIGS. 1A-1C).

For illustration purposes, we assumed equal amounts of informative allelic counts (the summation of fetus-specific and shared allelic counts) were obtained from chr21 and chrRef. Based on the above assumptions, 1,000 euploid and 1,000 T21 cases were simulated each time for different fractional fetal DNA concentrations to investigate the detection accuracy in both the paternally- and maternally-derived T21 models.

Figure 5:
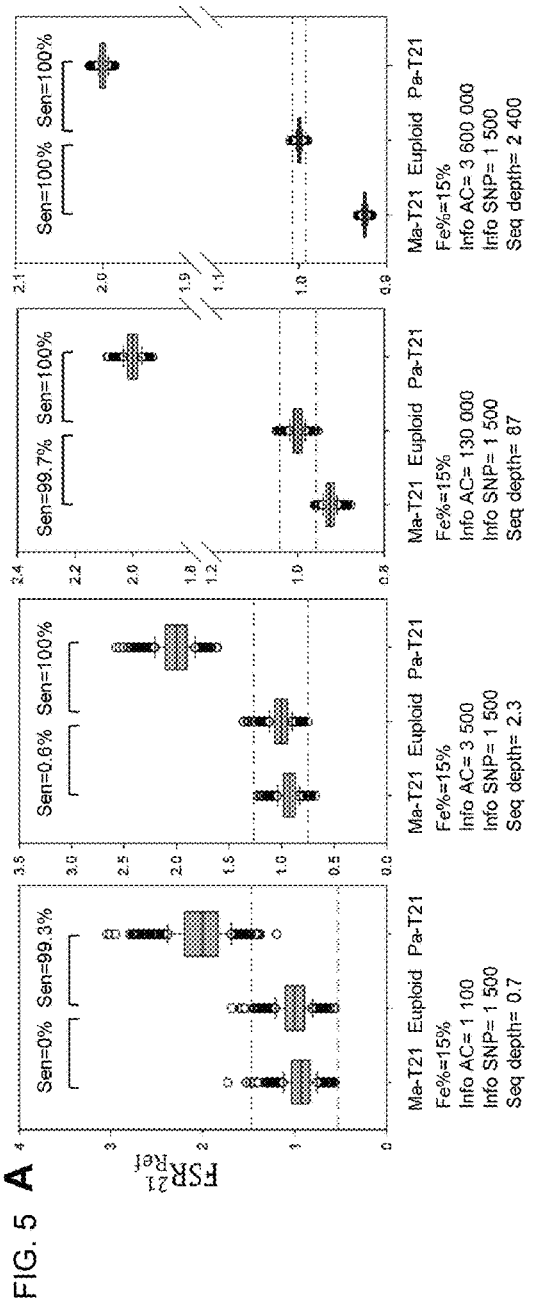
FIGS. 5A and 5B shows plots of a computer simulation for T21 detection for fractional fetal DNA concentrations of 5% (FIG. 5B) and 15% (FIG. 5A) according to embodiments of the present invention.
Figure 5:
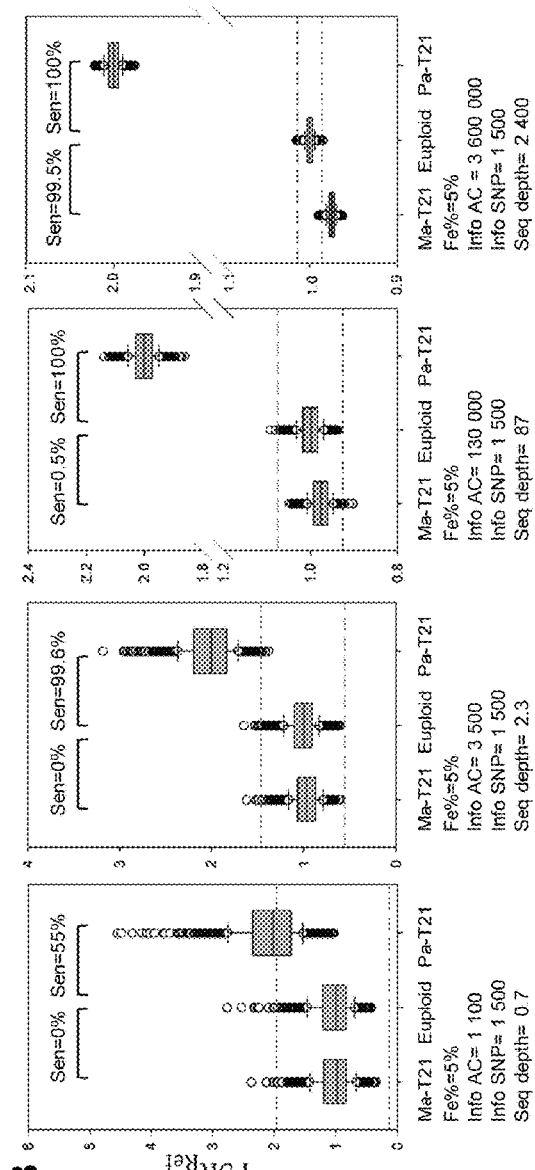

FIGS. 5A and 5B shows plots of a computer simulation for T21 detection for fractional fetal DNA concentrations of 5% (FIG. 5B) and 15% (FIG. 5A) according to embodiments of the present invention. We used computer simulation to determine the parameters that would further improve the accuracy of the allelic ratio approach for T21 detection. Computer simulation revealed relationships between the fetal DNA proportion, the number of informative alleles, and the depth of sequencing.

In order to obtain a specificity of greater than 99%, the cutoffs for T21 differentiation were chosen at 3 standard deviations above and below the mean F-S ratio of the euploid group. The sensitivity for paternally- and maternally-derived T21 detection was investigated on different numbers of informative allelic counts on chr21 and chrRef, respectively, for a fractional fetal DNA concentration of 15% (A). Similar analysis was performed for a fractional fetal DNA concentration of 5% (B). (Ma-T21: maternally-derived T21. Pa-T21: paternally-derived T21. Sen=sensitivity. Fe %=fractional fetal DNA concentration. Info AC=informative allelic counts on each of chr21 and chrRef. Info SNP=informative SNPs on each of chr21 and chrRef. Seq depth=sequencing depth. Info AC=Info SNP× Seq depth).

To get the plots of FIG. 5A, the fractional fetal DNA concentration was fixed at 15% and gradually increased the numbers of informative allelic counts on chr21 and chrRef to investigate the detection accuracy for fetal T21. Additional informative allelic counts would improve the detection accuracy in both the paternally- and maternally-derived T21 models. In order to obtain accurate detection (sensitivity >99%, specificity >99%), more informative allelic counts were required for the maternally-derived T21 detection (informative allelic counts=130,000) than the paternally-derived T21 detection (informative allelic counts=1,100) (FIG. 5A). If the fractional fetal DNA concentration was reduced to 5%, the corresponding informative allelic counts would need to be increased to 3,600,000 for detecting maternally-derived T21 and 3,500 for detecting paternally-derived T21 (FIG. 5B).

Figure 6:
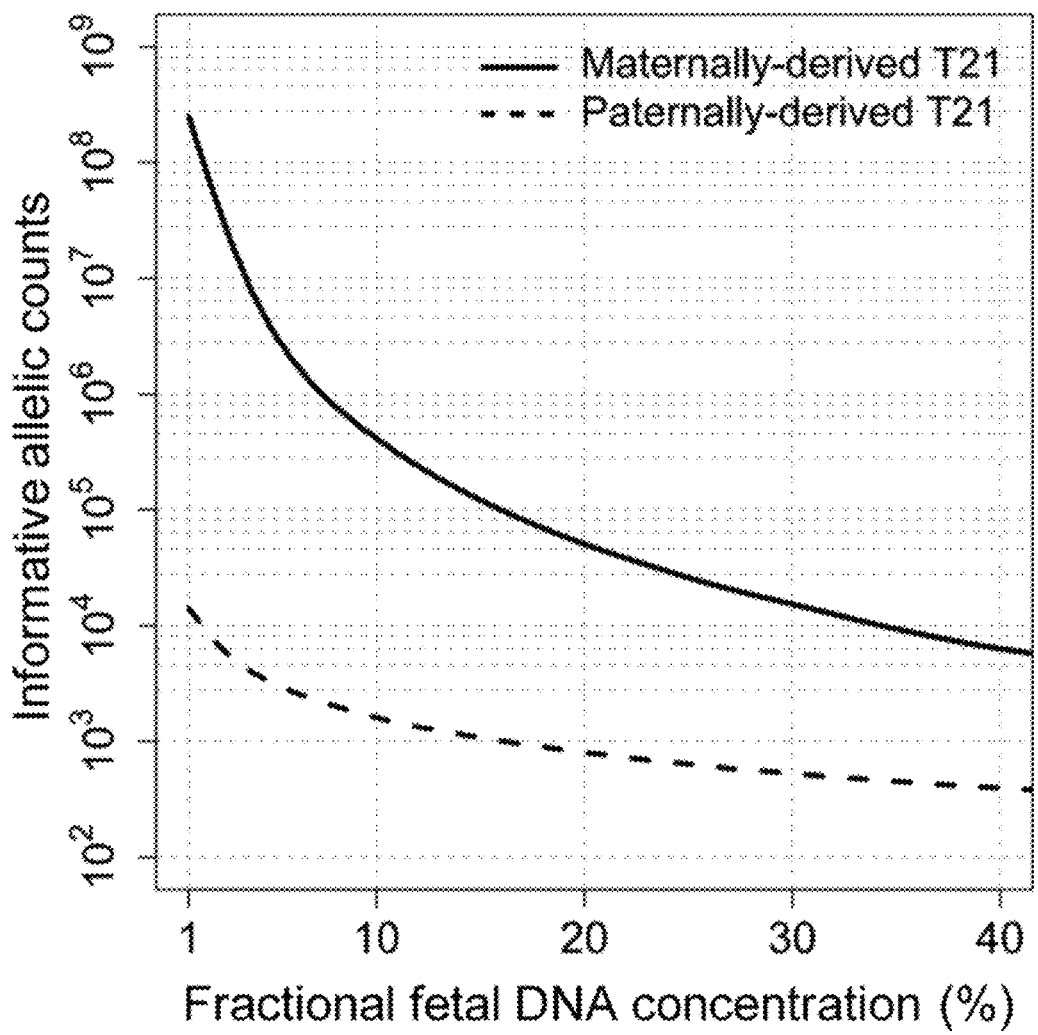
FIG. 6 shows a plot 600 of a computer simulation to investigate the minimal number of informative allelic counts for T21 detection.

FIG. 6 shows a plot 600 of a computer simulation to investigate the minimal number of informative allelic counts for T21 detection. The solid curve represents the minimal number of informative allelic counts required on each of chr21 and chrRef (Y axis), in order to achieve a reliable detection in maternally-derived T21 (sensitivity >99%, specificity >99%) according to a given fractional fetal DNA concentration (X axis). The dash curve represents the paternally-derived T21 model.

When the fractional fetal DNA concentration in maternal plasma was gradually decreased from 40% to 1%, the minimal number of informative allelic counts would need to be increased in both the paternally- and maternally-derived T21 scenarios, in order to maintain a high detection rate (sensitivity >99%, specificity >99%), but the count increase was more prominent for the maternally-derived T21 scenario. The sensitivity and specificity chosen for this analysis were chosen to mirror the recently reported performance of the non-polymorphic tag counting approach [12-14].

VII. Increasing Accuracy

As outlined above, there are various ways one could improve the detection accuracy. One approach is to increase the fractional concentration of fetal DNA, which would enlarge the magnitude of $FSR_{Ref}^{21}$ change in maternally-derived T21. Although an early study attempted to enrich the fetal DNA proportion by formaldehyde treatment of maternal plasma [7], this method is not ready for use because it has not been consistently reproduced by different groups [8-10]. Alternatively, the accuracy of detecting maternally-derived T21 can be improved by increasing the number of informative allelic counts. According to our simulation analysis, additional informative allelic counts would, to some extent, compensate for the loss of detection accuracy caused by the decrease in fractional fetal DNA concentration (FIG. 6). Two approaches can be used to increase the number of informative allelic counts, namely, recruiting more informative SNPs and sequencing each locus deeper. In one embodiment, both approaches are used.

A. Determining Informative Loci

The number of informative SNPs is generally determined by two factors: the total number of SNPs on the chromosome of interest for detection and the frequency of informative SNPs. The latter is the percentage of detectable informative SNPs amongst a group of analyzed SNPs. To investigate, the fetal genotype information, as determined by microarray-based analysis of chorionic villus DNA, was used to maximize the frequency of informative SNPs, the mean value of which is approximately 12% in all fourteen cases of this study. However, the fetal genomic material would not be available beforehand for actual NIPD. Therefore, informative SNPs would need to be deduced indirectly, for example, by selecting SNPs in which the parents are both homozygous but with different alleles (e.g., mother is AA and father is BB). In this scenario, the mean frequency of informative SNPs would decrease from 12% to 6%, because such an approach would exclude any SNPs in which the father is heterozygous.

In terms of SNP recruitment, a hybridization-based enrichment system may be used. In the examples above, we only employed a relatively small number of probes to capture 2,906 SNP loci on the target chromosomes. However, it is possible to increase the number of analyzed SNP loci. For example, if we design probes to cover all chr21 SNP loci (12,930 SNPs) on the Genome-Wide Human SNP Array 6.0 (Affymetrix), we could increase the number of informative SNPs on chr21 to approximately 1,500 SNPs for each case in the current dataset. If we obtain the same number of informative SNPs on chrRef and sequence the plasma DNA to a depth of 87 times, we would harvest approximately 130,000 informative allelic counts (1,500× 87) on chr21 and chrRef, respectively.

Such numbers would allow the relatively robust classification of maternally-inherited T21 from the euploid cases assuming a fractional fetal DNA concentration of 15% or above (FIG. 5A). Given that in this study the mean frequency of informative SNPs is approximately 12% and approximately 50% reads could be mapped back to the targeted regions (with the remaining reads being off-target), the total number of reads required to obtain 130,000 informative allelic counts would be approximately 4.3 million (130 000 reads×2/(12%×50%)).

However, if the fractional fetal DNA concentration is reduced to 5%, the number of reads would need to be increased to approximately 120 million (FIG. 5B). 5% and 15% were analyzed here because 5% is close to the lower limit for the non-polymorphism-based tag counting approach at the depth of sequencing used in a number of recent studies, and 15% is the approximate mean fractional fetal DNA concentration in the published clinical trials based on the tag counting approach [12-14].

B. Sequencing Deeper

In order to obtain sufficient number of allelic counts, an alternative approach is to sequence more deeply each locus with a relatively small number of informative SNPs. According to our previous publication, we demonstrated that each milliliter of plasma contained approximately 1,000 genome-equivalents of DNA, which would give rise to 2,000 allelic counts for each locus [4]. If we could count all of the alleles for each locus in 5 mL plasma, we would obtain 10,000 allelic counts for each locus. In this scenario, 26 informative SNPs (13 SNPs on chr21, 13 SNPs on chrRef) could provide sufficient informative allelic counts for maternally-derived T21 detection in a sample containing 15% fetal DNA, representing 130,000 informative allelic counts (10 000×13) on chr21 and chrRef, respectively. The number of informative SNPs would need to be increased to 720 (360 SNPs on chr21, 360 SNPs on chrRef) for a sample containing a fractional fetal DNA concentration of 5%. Due to the high read depth required by this strategy (i.e. 10,000 counts per informative allele), PCR-based approaches for target enrichment (i.e., amplification methods) might be alternative methods for this type of application [18,19].

VIII. Materials and Methods

We recruited fourteen pregnant women with singleton fetuses (gestational age ranging from 12 weeks to 13 weeks and 5 days). Maternal peripheral blood samples were collected prior to CVS. Following CVS, fetal genomic DNA samples were obtained from the chorionic villi. The aneuploidy or euploidy status were confirmed by full karyotyping. Among the fourteen cases, seven were T21 fetuses and the rest were euploid.

In one implementation, the DNA is extracted in the following way. Maternal peripheral blood samples (5-10 mL) were centrifuged at 1 600 g for 10 min at 4° C. The plasma portion (2-5 mL) was recentrifuged at 16 000 g for 10 min at 4° C. We removed any residual plasma from the blood cell portion by recentrifugation at 2 500 g for 5 min [16]. Plasma DNA was extracted with the DSP DNA Blood Mini Kit (Qiagen), as described previously [11]. Fetal and maternal genomic DNA was extracted from chorionic villi and peripheral blood cells, respectively, with the QIAamp DNA Blood Mini Kit (Qiagen) according to the manufacturer's protocol. The extracted plasma DNA was quantified by real-time PCR using an ABI 7300 Sequence Detector (Applied Biosystems). A β-globin real-time PCR assay was performed as described previously [4]. A conversion factor of 6.6 pg of DNA per cell was used to calculate the amount of the extracted plasma DNA.

A. Targeted Sequencing of Plasma DNA Libraries

The following is an example of sequencing techniques usable in embodiments. As the plasma DNA molecules were already fragmented in nature, no additional fragmentation step was required for this example. 10-30 ng plasma DNA for each case was used for DNA library construction by the Genomic DNA Sample Preparation Kit (Illumina) as previously described [15], except for the replacement of the adaptors and primers with the oligonucleotides from the Multiplexing Sample Preparation Oligonucleotide Kit (Illumina) and the SureSelect Target Enrichment System Kit (Agilent) according to the manufacturer's instructions.

In order to obtain high fold sequencing coverage for SNPs, the SureSelect Target Enrichment System (Agilent) was applied for capturing SNPs in the targeted regions. As a proof-of-principle study, approximately 5% of the probes were designed to target a total of 2 906 SNP loci on chr7 (313 SNPs), chr13 (564 SNPs), chr18 (592 SNPs) and chr21 (1 437 SNPs), while the remaining probes were designed for another project. 500 ng of each constructed plasma DNA library was incubated with the probes for 24 h at 65° C. After hybridization, the captured DNA molecules were eluted and amplified by a 12-cycle PCR according to manufacturer's instructions. Libraries with and without target enrichment were indexed for multiplex sequencing on a Genome Analyzer IIx (Illumina) in 50-bp×2 paired-end format. An additional 7 cycles of sequencing were performed to decode the index sequence.

All sequenced reads were aligned to the unmasked human reference genome (Hg18) (genome.ucsc.edu) with the aid of SOAPaligner/soap2 (soap.genomics.org.cn). Two mismatches were allowed during alignment. The range of fragment sizes of paired-end reads was defined as 50-600 bp. Duplicated paired-end reads (e.g., reads with identical sequences and start-end coordinates) were considered clones of the same original plasma DNA template. All but one of the duplicated reads were filtered, leaving only 1 copy for subsequent bioinformatics analysis as previously described [15].

B. Microarray Genotyping

Genotyping was used to confirm the accuracy of the sequencing techniques. Maternal and fetal genomic DNA samples were genotyped with the Genome-Wide Human SNP Array 6.0 (Affymetrix). The parental origin of the additional copy of chr21 in seven T21 fetuses was determined using microarray analysis of the chorionic villus samples in which the allelic signal intensities for SNPs on chr21 were analyzed. If the fetus has paternally-derived T21, the signal intensity of the fetus-specific allele (B allele) should be 2-fold higher than the shared allele (A allele), because the fetal genotype would become ABB on chr21, and vice versa. Using this approach, one fetus was identified as a paternally-derived T21, while six were maternally-derived T21.

IX. Computer System

Figure 7:
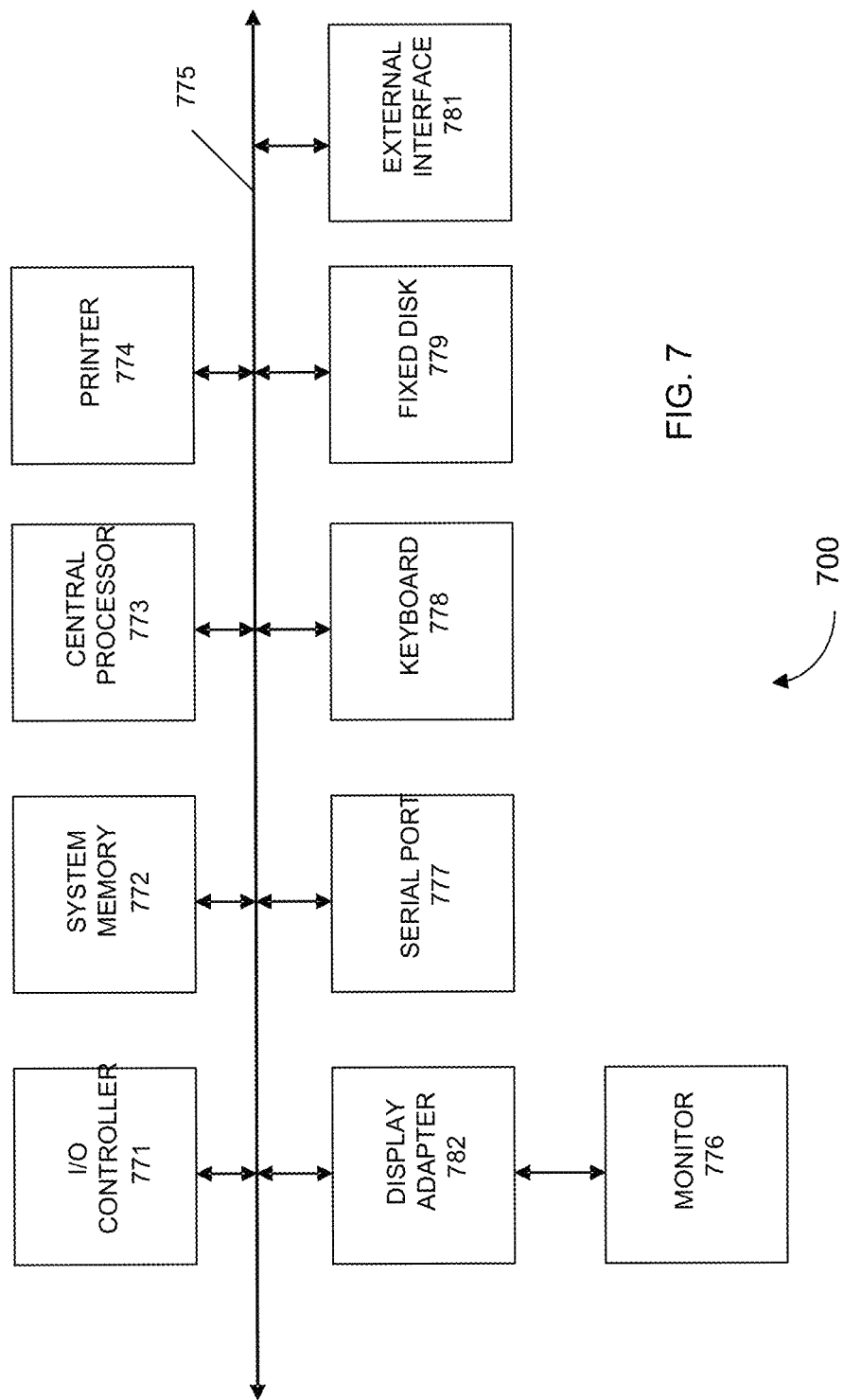
FIG. 7 shows a block diagram of an example computer system 700 usable with system and methods according to embodiments of the present invention.

Any of the computer systems mentioned herein may utilize any suitable number of subsystems. Examples of such subsystems are shown in FIG. 7 in computer apparatus 700. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 7 are interconnected via a system bus 775. Additional subsystems such as a printer 774, keyboard 778, fixed disk 779, monitor 776, which is coupled to display adapter 782, and others are shown. Peripherals and input/output (I/O) devices, which couple to I/O controller 771, can be connected to the computer system by any number of means known in the art, such as serial port 777. For example, serial port 777 or external interface 781 (e.g. Ethernet, Wi-Fi, etc.) can be used to connect computer system 700 to a wide area network such as the Internet, a mouse input device, or a scanner. The interconnection via system bus 775 allows the central processor 773 to communicate with each subsystem and to control the execution of instructions from system memory 772 or the fixed disk 779, as well as the exchange of information between subsystems. The system memory 772 and/or the fixed disk 779 may embody a computer readable medium. Any of the values mentioned herein can be output from one component to another component and can be output to the user.

A computer system can include a plurality of the same components or subsystems, e.g., connected together by external interface 781 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned herein are incorporated by reference in their entirety for all purposes. None is admitted to be prior art.

REFERENCES

1. Driscoll D A, Gross S (2009) Prenatal screening for aneuploidy. N Engl J Med 360: 2556-2562.
2. Mujezinovic F, Alfirevic Z (2007) Procedure-related complications of amniocentesis and chorionic villous sampling: a systematic review. Obstet Gynecol 110: 687-694.
3. Lo Y M D, Corbetta N, Chamberlain P F, Rai V, Sargent I L, et al. (1997) Presence of fetal DNA in maternal plasma and serum. Lancet 350: 485-487.
4. Lo Y M D, Tein M S C, Lau T K, Haines C J, Leung T N, et al. (1998) Quantitative analysis of fetal DNA in maternal plasma and serum: implications for noninvasive prenatal diagnosis. Am J Hum Genet 62: 768-775.
5. Tong Y K, Ding C M, Chiu R W K, Gerovassili A, Chim S S C, et al. (2006) Noninvasive prenatal detection of fetal trisomy 18 by epigenetic allelic ratio analysis in maternal plasma: theoretical and empirical considerations. Clin Chem 52: 2194-2202.
6. Lo Y M D, Tsui N B Y, Chiu R W K, Lau T K, Leung T N, et al. (2007) Plasma placental RNA allelic ratio permits noninvasive prenatal chromosomal aneuploidy detection. Nat Med 13: 218-223.
7. Dhallan R, Guo X, Emche S, Damewood M, Bayliss P, et al. (2007) A non-invasive test for prenatal diagnosis based on fetal DNA present in maternal blood: a preliminary study. Lancet 369: 474-481.
8. Benachi A, Yamgnane A, Olivi M, Dumez Y, Gautier E, et al. (2005) Impact of formaldehyde on the in vitro proportion of fetal DNA in maternal plasma and serum. Clin Chem 51: 242-244.
9. Chinnapapagari S K R, Holzgreve W, Lapaire O, Zimmermann B, Hahn S (2005) Treatment of maternal blood samples with formaldehyde does not alter the proportion of circulatory fetal nucleic acids (DNA and mRNA) in maternal plasma. Clin Chem 51: 652-655.
10. Chung G T Y, Chiu R W K, Chan K C A, Lau T K, Leung T N, et al. (2005) Lack of dramatic enrichment of fetal DNA in maternal plasma by formaldehyde treatment. Clin Chem 51: 655-658.
11. Chiu R W K, Chan K C A, Gao Y A, Lau V Y M, Zheng W L, et al. (2008) Noninvasive prenatal diagnosis of fetal chromosomal aneuploidy by massively parallel genomic sequencing of DNA in maternal plasma. Proc Natl Acad Sci USA 105: 20458-20463.
12. Chiu R W K, Akolekar R, Zheng Y W L, Leung T Y, Sun H, et al. (2011) Non-invasive prenatal assessment of trisomy 21 by multiplexed maternal plasma DNA sequencing: large scale validity study. BMJ 342: 9.
13. Palomaki G E, Kloza E M, Lambert-Messerlian G M, Haddow J E, Neveux L M, et al. (2011) DNA sequencing of maternal plasma to detect Down syndrome: an international clinical validation study. Genet Med 13: 913-920.
14. Bianchi D W, Platt L D, Goldberg J D, Abuhamad A Z, Sehnert A J, et al. (2012) Genome-wide fetal aneuploidy detection by maternal plasma DNA sequencing. Obstet Gynecol. In press. doi: 10.1097/AOG.0b013e31824fb482
15. Liao G J W, Lun F M F, Zheng Y W L, Chan K C A, Leung T Y, et al. (2011) Targeted massively parallel sequencing of maternal plasma DNA permits efficient and unbiased detection of fetal alleles. Clin Chem 57: 92-101.
16. Chiu R W K, Poon L L M, Lau T K, Leung T N, Wong E M C, et al. (2001) Effects of blood-processing protocols on fetal and total DNA quantification in maternal plasma. Clin Chem 47: 1607-1613.
17. Antonarakis S E (1991) Parental origin of the extra chromosome in trisomy 21 as indicated by analysis of DNA polymorphisms. N Engl J Med 324: 872-876.
18. Mamanova L, Coffey A J, Scott C E, Kozarewa I, Turner E H, et al. (2010) Target-enrichment strategies for next-generation sequencing. Nat Methods 7: 111-118.
19. Tewhey R, Warner J B, Nakano M, Libby B, Medkova M, et al. (2009) Microdroplet-based PCR enrichment for large-scale targeted sequencing. Nat Biotechnol 27: 1025-1031.
20. Albert T J, Molla M N, Muzny D M, Nazareth L, Wheeler D, Song X, et al. (2007) Direct selection of human genomic loci by microarray hybridization. Nat Methods; 4:903-5.
21. Gnirke A, Melnikov A, Maguire J, Rogov P, LeProust E M, Brockman W, et al. (2009) Solution hybrid selection with ultra-long oligonucleotides for massively parallel targeted sequencing. Nat Biotechnol; 27:182-9.

What is claimed is:

1. A method of analyzing a biological sample from a female subject pregnant with a fetus to determine whether the fetus has an aneuploidy associated with a first chromosome, the biological sample containing a mixture of cell-free DNA molecules from the fetus and the female subject, the method comprising:

enriching the biological sample for DNA molecules from a plurality of target regions that are known to have polymorphic loci;

after the enriching, sequencing the DNA molecules from the biological sample to obtain a plurality of sequence reads;

analyzing, by a computer system, the plurality of sequence reads, wherein analyzing a sequence read includes:
  identifying a location of the sequence read in a reference genome by aligning the sequence read to the reference genome; and
  determining a respective allele of the sequence read;

identifying, by the computer system, a plurality of first loci on the first chromosome, the plurality of first loci corresponding to a portion of the target regions;

identifying, by the computer system, a plurality of second loci on one or more reference chromosomes, the plurality of second loci corresponding to a portion of the target regions, wherein the pregnant female is homozygous for a respective maternal allele at each of the first and second loci, and wherein the fetus is heterozygous for the respective maternal allele and a respective paternal allele at each of the first and second loci, the respective paternal alleles being different from the respective maternal alleles;

determining, by the computer system, a first maternal amount of the respective maternal alleles at the plurality of first loci;

determining, by the computer system, a first paternal amount of the respective paternal alleles at the plurality of first loci;

calculating a first ratio of the first maternal amount and the first paternal amount;

determining, by the computer system, a second maternal amount of the respective maternal alleles at the plurality of second loci;

determining, by the computer system, a second paternal amount of the respective paternal alleles at the plurality of second loci;

calculating a second ratio of the second maternal amount and the second paternal amount;

calculating a third ratio of the first ratio and the second ratio; and comparing the third ratio to one or more cutoff values to determine whether the fetus has an aneuploidy associated with the first chromosome, wherein a first cutoff value of the one or more cutoff values corresponds to an aneuploidy that is paternally-derived.

2. The method of claim 1, wherein enriching the biological sample includes:
capturing the DNA molecules of the biological sample with immobilized probes corresponding to the plurality of target regions.

3. The method of claim 1, wherein enriching the biological sample includes:
amplifying the DNA molecules of the biological sample with primers corresponding to the plurality of target regions.

4. The method of claim 1, wherein identifying a first locus of the plurality of first loci on the first chromosome includes:
aligning a plurality of sequence reads to the first locus; and
identifying two alleles among the plurality of sequence reads aligned to the first locus.

5. The method of claim 4, further comprising:
determining a first number of sequence reads corresponding to a first allele at the first locus;
determining a second number of sequence reads corresponding to a second allele at the first locus;
calculating an allelic ratio of the first number and the second number;
determining whether the allelic ratio is above a first threshold and below a second threshold.

6. The method of claim 1, wherein identifying a first locus of the plurality of first loci on the first chromosome includes:
identifying that the father of the fetus is homozygous for a first allele at the first locus; and
identifying that the pregnant female is homozygous for a second allele at the first locus.

7. The method of claim 1, wherein the first ratio is a first percentage as determined from the first maternal amount and the first paternal amount, and wherein the second ratio is a second percentage as determined from the second maternal amount and the second paternal amount.

8. The method of claim 1, wherein the first ratio includes the first paternal amount divided by a sum of the first paternal amount and the first maternal amount.

9. The method of claim 1, wherein the first ratio includes the first paternal amount divided by the first maternal amount, and the second ratio includes the second paternal amount divided by the second maternal amount.

10. The method of claim 1, wherein:
the third ratio is the first ratio divided by the second ratio, and
a second cutoff value of the one or more cutoff values corresponds to an aneuploidy that is maternally-derived.

11. The method of claim 10, wherein comparing the third ratio to one or more cutoff values includes:
comparing the third ratio to the first cutoff value to determine whether the fetus has a paternally-derived aneuploidy, the method further comprising:
when the fetus does not have a paternally-derived aneuploidy:
measuring a fractional fetal DNA concentration in the mixture; and
comparing the third ratio to the second cutoff value to determine whether the fetus has a maternally-derived aneuploidy, wherein the second cutoff value is determined using the fractional fetal DNA concentration.

12. The method of claim 10, wherein the third ratio is approximately two when the aneuploidy is paternally-derived.

13. The method of claim 10, wherein the third ratio is approximately $1-(f/2)$ when the aneuploidy is maternally-derived, where f is a fractional fetal DNA concentration in the mixture.

14. The method of claim 13, further comprising:
determining the fractional fetal DNA concentration f from the second paternal amount and the second maternal amount.

15. The method of claim 1, wherein the first chromosome is chromosome 21, chromosome 13, or chromosome 18.

16. The method of claim 1, wherein at least one of the first loci is a SNP.

17. The method of claim 1, wherein the plurality of second loci are located on a plurality of reference chromosomes.

18. The method of claim 1, further comprising:
obtaining a blood sample from the female subject; and
extracting plasma or serum from the blood sample to obtain the biological sample.

19. The method of claim 6, wherein identifying that the father of the fetus is homozygous for the first allele at the first locus comprises genotyping the father of the fetus at the first locus, and
wherein identifying that the pregnant female is homozygous for the second allele at the first locus comprises genotyping the pregnant female at the first locus using a sample from the pregnant female.

20. The method of claim 19, wherein the sample from the pregnant female includes blood cells from the pregnant female.

* * * * *